United States Patent [19]

Hanagan et al.

[11] Patent Number: 5,520,787

[45] Date of Patent: May 28, 1996

[54] DIAGNOSTIC FLOW CELL DEVICE

[75] Inventors: Ted J. Hanagan, Libertyville; Lance K. Safford, Park City; Steven G. Schultz, Winthrop Harbor; Jay R. Ford, Mt. Prospect; Edmund T. Marciniec, Libertyville; Kenneth S. Johnson, Buffalo Grove; John D. Norlie, Jr., Gurnee, all of Ill.

[73] Assignee: Abbott Laboratories, Abbott Park, Ill.

[21] Appl. No.: 400,412

[22] Filed: Mar. 3, 1995

Related U.S. Application Data

[63] Continuation of Ser. No. 194,652, Feb. 9, 1994, abandoned.

[51] Int. Cl.$^6$ .................................................. G01N 27/26
[52] U.S. Cl. ..................... 204/409; 204/403; 204/412; 204/415; 422/82.01; 422/82.02; 422/68.1; 435/817; 435/287.1; 435/287.7; 435/287.9; 205/777.5
[58] Field of Search ................................. 204/403, 409, 204/412, 153.12, 415, 418; 422/82.06, 82.07, 82.08, 82.09, 82.01, 82.02, 68.1; 435/817, 288, 291

[56] References Cited

U.S. PATENT DOCUMENTS

| | | | |
|---|---|---|---|
| 4,950,379 | 8/1990 | Young et al. | 204/403 |
| 4,963,245 | 10/1990 | Weetall | 204/403 |
| 4,999,582 | 3/1991 | Parks et al. | 324/438 |
| 5,030,310 | 7/1991 | Wogoman | 156/252 |
| 5,043,286 | 8/1991 | Khalil et al. | 128/634 |
| 5,096,836 | 3/1992 | Macho et al. | 436/169 |
| 5,200,051 | 4/1993 | Cozzette et al. | 204/403 |
| 5,264,103 | 11/1993 | Yoshioka et al. | 204/403 |
| 5,284,568 | 2/1994 | Pace et al. | 204/403 |
| 5,422,246 | 6/1995 | Koopal et al. | 204/403 |

FOREIGN PATENT DOCUMENTS

| | | |
|---|---|---|
| 0327018 | 9/1989 | European Pat. Off. . |
| 0537761 | 4/1993 | European Pat. Off. . |
| 0569908 | 11/1993 | European Pat. Off. . |
| WO8803270 | 5/1988 | WIPO . |
| WO9304359 | 3/1993 | WIPO . |

OTHER PUBLICATIONS

H. Allen O. Hill, et al., *Enzyme Dual–Electrode for Analyte Determination*, Anal. Chem., 1989 61, 2200–2206. no month available.

N. A. Morris, et al., *An Electrochemical Capillary Fill Device for the Analysis of Glucose Incorporating Glucose Oxidase and Ruthenium (III) Hexamine as Mediator*, Electroanalysis, 4 (1992) 1–9. no month available.

Ph. Arquint, et al., *Integrated blood–gas sensor for $pO_2$, $pCO_2$ and pH*, Sensors and Actuators E 13–14 (1993) 340–344. no month available.

(List continued on next page.)

*Primary Examiner*—Bruce F. Bell

[57] ABSTRACT

The present invention provides a diagnostic flow cell for determining the presence or amount of an analyte which may be contained in a test sample. The flow cell comprises a spacing layer having a longitudinal void disposed between a pair of opposed substrates. The spacing layer and the opposed substrates define a flow channel wherein reagent means can be immobilized. When the immobilized reagent means is contacted with an analyte, the reagent means can produce an electrically, optically, or electrically and optically detectable response to the analyte. Hence, the reagent means that is immobilized within the flow channel can comprise (i) a counter electrode, a reference electrode and a working electrode, (ii) an optically sensitive dye or (iii) a counter electrode, a reference electrode and a working electrode and an optically sensitive dye. The flow cell can be interfaced with means for introducing a test sample into and out of the flow cell's flow channel and detection means for detecting a signal generated by the immobilized reagent means.

The present invention also provides methods for detecting the presence or amount of an analyte which may be contained in a test sample.

39 Claims, 5 Drawing Sheets

OTHER PUBLICATIONS

S. Alegret, et al., *Flow–Through pH–ISFET as Detector in Automated Determinations,* Electroanalysis, 3 (1991) 349–354. no month available.

B. H. van der Schoot, et al., *A modular miniaturized chemical analysis system,* Sensors and Actuators B. 13–14 (1993) 333–335. no month available.

G. Urban, et al., *Miniaturized multi–enzyme biosensors integrated with pH sensors on flexibl polymer carriers for in vivo applications,* Biosensors & Bioelectronics, 7 (1992) 733–739. no month available.

M. A. Genshaw, et al., *Whole Blood Glucose Enzyme Electrode,* J. Electrochem. Soc., vol. 136, No. 2, Feb. 1989 @ The Electrochemical Society, Inc.

W. J. Bowyer, et al., *Electrochemical Measurements in Submicroliter Volumes,* Anal. Chem., 1992, 64, 459–462. no month available.

C–Yuan Chen, et al., *Amperometric needle–type glucose sensor based on a modified platinum electrode with diminished response to interfeing materials,* Analytica Chimica Acta, 265 (1992) 5–14. no month available.

$f(x) = 2.622951E+2*x + 1.497951E+2$
$R^2 = 9.880593E-1$

DIAGNOSTIC FLOW CELL DEVICE

This is a continuation of application Ser. No. 08/194,652 filed on Feb. 9, 1994, now abandoned.

FIELD OF THE INVENTION

The present invention relates to a flow cell device for detecting the presence or amount of an analyte in a test sample. In particular, the present invention relates to a flow cell device having immobilized reagent means which produce an electrically or optically detectable response to an analyte which may be contained in a test sample.

BACKGROUND OF THE INVENTION

Immobilized catalytically-active-molecules such as enzymes have been used as binding participants to determine the presence or amount of the immobilized enzyme's substrate that may be present in a test sample. Commercial chemistry analyzers use enzymes, which have been bound to porous surfaces, for the conversion of enzyme substrates to optically or electrochemically detectable products. For example, electrochemical sensors utilize the ability of an immobilized enzyme to form an electrochemically active molecule as a result of the action of the enzyme on its substrate. Such sensors employ a potentiostat and amperometric electrodes that typically consist of an enzyme or working electrode, a reference electrode and a counter electrode. The enzyme electrode is typically made of platinum and is supplied with an overlaying oxidase enzyme layer. When the surface of an electrode is immersed in a sample containing an oxidizable substrate and molecular oxygen, both molecules diffuse into the enzyme layer where the substrate reacts with the enzyme resulting in reduction of the enzyme. The reduced enzyme is oxidized by the molecular oxygen which, in turn, is reduced to peroxide. At a sufficiently high electrode potential (maintained via the reference electrode), the platinum portion of the enzyme electrode oxidizes the peroxide to regenerate oxygen and transfer two electrons to the counter electrode. The potentiostat measures the current generated by the transferred electrons and the amount of current is related to the amount of oxidizable substrate in the sample. Hence, the presence and/or amount of an oxidizable substrate in the sample can be determined.

Prior to the present invention, devices which electrochemically or optically detect the presence or amount of an analyte which may be present in a test sample are generally single use disposable devices which are incapable of analyzing a plurality of circulating test samples.

SUMMARY OF THE INVENTION

According to the present invention, a diagnostic flow cell for determining the presence or amount of an analyte in a test sample is provided. The diagnostic flow cell comprises (i) a spacing layer disposed between a first and a second opposed substrate, wherein the spacing layer has a longitudinal void and wherein the spacing layer and opposed substrates define a flow channel; (ii) fastening means for coupling the spacing layer and the opposed substrates; (iii) inlet means for permitting a sample to enter the flow channel; (iv) outlet means for permitting the sample to exit the flow channel; and (v) immobilized reagent means for producing a detectable signal, wherein the reagent means is at least partially contained within the flow channel. Using methods well known in the art, the flow cell can be interfaced with detection means for detecting a signal generated by the immobilized reagent means. Additionally, methodologies are well known in the art for placing the flow cell in fluid communication with flow means for introducing a test sample into the flow cell's flow channel.

The immobilized reagent means can comprise (i) a counter electrode, a reference electrode and a working electrode or (ii) an optically sensitive dye. Advantageously, combinations of the reagent means can be employed.

The present invention also provides methods for detecting the presence or amount of an analyte which may be contained in a test sample. According to one embodiment of the invention, the flow cell device can generate an electrically detectable response to an analyte that may be present in a test sample.

According to another embodiment of the invention, the assay device can generate an optically detectable response to an analyte that may be present in a test sample.

According to still another embodiment of the invention, the assay device can generate optically and electrochemically detectable responses to analytes which may be present in a test sample.

Due to the low costs associated with the manufacture of the flow cell, it can be used as a disposable assay unit. However the present invention provides an assay device that can be used for multiple assays and is thereby reusable.

DETAILED DESCRIPTION OF THE INVENTION

Figure 1:
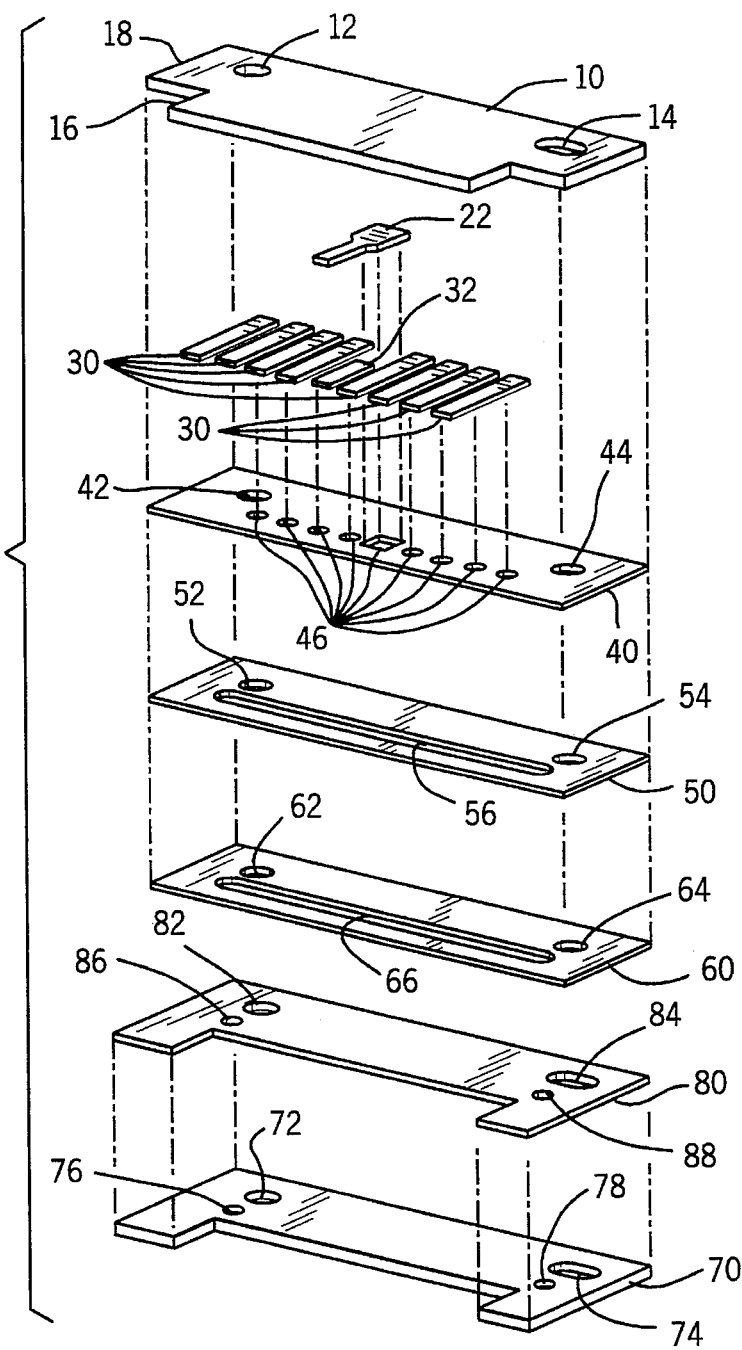
FIG. 1 illustrates an expanded view of an electrochemical flow cell.

The following definitions are applicable to the invention:

I. DEFINITIONS

The term "analyte", as used herein, refers to the compound or composition to be detected or measured and which initiates the generation of a detectable response. Analytes include, but are not intended to be limited to, enzymes or enzyme substrates, metal ions, blood gases, toxins, organic compounds, proteins, peptides, amino acids, carbohydrates, nucleic acids, hormones, steroids, vitamins, drugs (including those administered for therapeutic purposes as well as those administered for illicit purposes), and metabolites of any of the above substances. For example, such analytes include, but are not intended to be limited to, alanine aminotransferase (ALT), aspartate aminotransferase (AST), creatinine kinase (CK), creatinine kinase MB (CK-MB), lactate dehydrogenase (LDH), gamma glutamyl transpeptidase (GGTP), alkaline phosphatase, glucose, fructose, galactose, sucrose, lactose, lactate, cholesterol, urea, creatinine, triglycerides, uric acid, bilirubin, glutamate, potassium, sodium, chloride, calcium, magnesium, lithium, oxygen, carbon dioxide, hydrogen ions (pH), hemoglobin, glycated hemoglobin (Gly. Hb), C-reactive protein, serum lipoproteins, serum albumin, deoxyribonucleic acid (DNA), ribonucleic acid (RNA), bile acids, salicylates, acetaminophen, theophylline, phenytoin and the like.

The term "test sample", as used herein, refers to a material suspected of containing the analyte. The test sample can be used directly as obtained from the source or following a pre-treatment to modify the character of the sample. The test sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid and the like, and fermentation broths cell cultures, and chemical reaction mixtures and the like. The test sample can be pretreated prior to use, such as preparing plasma from blood, diluting viscous fluids, and the like. Methods of treatment can involve filtration, distillation, concentration, inactivation of interfering components, and the addition of reagents. In addition to biological or physiological fluids, other liquid samples can be used such as water, food products and the like for the performance of environmental or food production assays. In addition, a solid material suspected of containing the analyte can be used as the test sample. In some instances, it may be beneficial to modify a solid test sample to form a liquid medium or to release the analyte.

II. FLOW CELLS

The present invention is directed to a diagnostic flow cell comprising two opposed substrate layers and a spacing or gasket layer disposed between the two opposed substrate layers. The spacing or gasket layer has a longitudinal void which, in combination with the substrates, defines the flow cell's flow channel. A substrate layer, or the substrate layers, can be supplied with apertures which, when the flow cell is assembled, can serve as inlet and outlet means for introducing sample into the flow channel and allowing sample to exit the flow channel. Preferably, the apertures are supplied to one substrate and are located near the ends of the flow channel defined by the substrates and the spacing layer.

Reagent means that can generate a detectable signal when contacted with an analyte can be immobilized on a substrate or the substrates. Typically, the immobilized reagent means is substantially insoluble. Consequently, the reagent means can be contacted with multiple test samples thereby making the flow cell reusable. Depending upon the analyte to be detected, the opposed substrates can have a single or multiple reagent means immobilized thereon. Thus, by immobilizing the appropriate reagent means, a single flow cell can, for example, electrically and optically detect analytes which may be present in a test sample. Additionally, by immobilizing a multiplicity of the same reagent means to a substrate or the substrates, a single flow cell can detect the presence or amount of an analyte in replicates.

The various layers that can comprise the flow cell herein provided can be applied to the opposed substrates, and the substrates can then be coupled with a gasket layer to thereby form the flow cell taught herein. Due to the design of the flow cell and the manner in which it can be manufactured, the diagnostic flow cell is reusable, inexpensive to produce, easily stored in a complete or incomplete form, capable of being patterned with immobilized reagent means, and, as compared to previous technology, the number of machined parts is greatly reduced. Moreover, signal to noise ratios which are generated by the reagent means are increased and electromagnetic interferences are reduced.

The opposed substrates can be made of any chemically inert, non-conductive and physically durable material which is capable of supporting the various materials applied thereon. Examples of such materials include, but are not intended to be limited to film plastics such as polyester, polycarbonate, polystyrene, polyetherimide, and the like; molded plastics such as acrylic, phenolic, polyolefin, and the like; ceramics such as alumina ($Al_2O_3$), zirconia ($ZrO_2$), magnesia (MgO), and the like; glass; silicon wafers; and the like; preferably the substrate material comprises a polyester film.

The spacing or gasket layer materials are typically chemically and electrochemically inert as well as substantially non-absorbent and impervious to water. Examples of materials that have these properties include, but are not intended to be limited to printing inks, painted inks, sprayed inks, latexes, urethanes, vinyls, polyesters, film plastics and the like, preferably the spacing layer comprises a dielectric printing ink. The thickness of the flow cell's spacing layer is largely responsible for the volume of the flow channel. Thus, for example, when it is desirable to have large amounts of sample contained within the flow channel, the thickness of the spacing layer can be increased. The amount of sample contained in the flow channel, in relation to the exposed substrate surface area, is preferably in the range of between about 1.0 $\mu l/cm^2$ and about 500 $\mu l/cm^2$, more preferably between about 2 $\mu l/cm^2$ and about 250 $\mu l/cm^2$ and most preferably between about 2.5 $\mu l/cm^2$ and about 100 $\mu l/cm^2$.

The diagnostic flow cell can further comprise a mask layer immobilized between the two substrate layers. Similarly to the spacing layer, the mask layer is typically chemically and electrochemically inert as well as non-absorbent and impervious to water. Examples of suitable mask layer materials have been described with reference to the spacing layer. When multiple analytes are to be detected, or replicates of the same analyte are to be detected, the mask layer is particularly preferred and serves as a barrier between the various immobilized reagent means.

The opposed substrates, and the various layers that can be disposed between the substrates, can be secured or coupled to one another to form a flow cell using fastening means such as, for example, lamination, solvent bonding, nuts and bolts, rivets and the like, preferably an adhesive layer secures the substrates, and the various layers thereon, to each other. An adhesive layer is preferably inert chemically and electrochemically as well as being capable of retaining its adherent quality in saline solutions. Examples of such materials include, but are not limited to ultraviolet cured pressure sensitive adhesives, heat cured pressure sensitive adhesives, vinyl based pressure sensitive adhesives, and the like, preferably a polyurethane based ultravioletly cured adhesive.

A. ELECTROCHEMICAL FLOW CELLS

In the case where the diagnostic flow cell is capable of electrochemically detecting an analyte that may be contained in a test sample, the substrates can have reagent means immobilized thereon which form a reference electrode, a counter electrode and a working electrode. The reference electrode can comprise (i) a material or a combination of materials capable of stabilizing a test sample's potential or otherwise providing a constant potential within a test solution; and (ii) a conductive trace material which is capable of being interfaced with a detection means and which is substantially inert at the assay device's operating potential. Materials capable of developing a stable potential include oxidation/reduction pairs (variably referred to as "redox couples") including, but not intended to be limited to, silver/silver chloride/graphite blends, mercury/mercurous chloride blends, silver/silver iodide blends and the like, preferably silver/silver chloride blends which can be dispensed using screen printing techniques. Examples of materials that can be used as conductive trace material include, but are not intended to be limited to gold, carbon, nickel, silver, palladium, ruthenium, rhodium, tin oxide, indium tin oxide and the like, preferably carbon that has been dispersed in a screen printing ink.

The counter electrode can comprise an electrochemically conductive material which is relatively inert at the assay device's operating potential. Examples of materials having these properties include, but are not intended to be limited to gold, carbon, nickel, silver, palladium, ruthenium, rhodium, tin oxide, indium tin oxide and the like, preferably carbon that has been dispersed in a screen printing ink.

The working electrode can comprise (i) a conductive trace material and ii) an enzyme or enzymes immobilized to or in contact with the conductive trace. Preferably, the enzyme is immobilized on the conductive trace such that when the flow cell is assembled, the enzyme will remain efficacious for multiple uses. A particularly preferred method of immobilizing an enzyme to the conductive trace material employs an immobilization medium disclosed in co-owned and co-pending application Ser. No. 08/193,972, entitled BIOREAGENT IMMOBILIZATION MEDIUM, filed on even date herewith and incorporated herein by reference.

The bioreagent immobilization medium comprises i) an enzyme which is immobilized to a solid phase and ii) a binding reagent comprising a latex resin, wherein the immobilized enzyme is evenly dispersed. The binding reagent may also include optional ingredients which enhance the immobilization medium's chemical and physical properties. The enzyme can be immobilized to the solid phase by methods well known in the art such as, for example, covalent, ionic or adsorptive bonding of the enzyme to the solid phase. By way of example and not of limitation, the various enzymes, solid phases, resins and optional ingredients that can be employed in the bioreagent immobilization medium can be found below in Table 1.

In order to allow easy interface with detection means for detecting a signal generated by the immobilized reagent means, it is preferred that a portion of the immobilized reagent means is contained within the flow channel and a portion of the immobilized reagent means extends out of the flow cell's flow channel.

It will be understood, of course, that the present invention is not limited to flow cells having three electrode systems, and that two electrode systems are contemplated. For example, a two electrode configuration can comprise a working electrode and a combination reference/counter electrode.

B. OPTICAL FLOW CELLS

In cases where the diagnostic flow cell optically detects the presence or amount of an analyte which may be contained in a test sample, the immobilized reagent means generates an optically detectable signal when it is contacted with an analyte which may be contained in a test sample. The immobilized reagent means that can be used in optically based flow cells are generally compounds or mixtures of compounds that, when contacted with an analyte, emit a signal which is optically detectable. Examples of such immobilized reagent means include, but are not intended to be limited to pH sensitive dyes; oxygen sensitive dyes; dyes or chelating agents which are sensitive to ions such as calcium and magnesium ions; and the like; preferably platinum tetra(pentafluorophenyl)porphyrin which is an oxygen sensitive dye that changes its fluorescence lifetime in the presence of dissolved oxygen. Such an optically sensitive dye is disclosed in U.S. Pat. No. 4,810,655 and U.S. Pat. No. 5,043,286 both of which are herein incorporated by reference.

Optical flow cell devices preferably have the immobilized reagent means entirely contained within the flow cell's flow channel, and such a flow cell is configured to be interfaced with a detection means using optical fibers, optical wave guides, incident beams of light, and the like.

C. MULTIPLE APPLICATION FLOW CELLS

As it will be understood by one skilled in the art, multiple reagent means can be immobilized to the substrate or substrates. Consequently, a single flow cell can optically and electrochemically detect the presence or amount of an analyte or multiple analytes which may be contained in a test sample.

III. FLOW CELL PRODUCTION

The flow cell can be manufactured by layering the opposed substrates with the various layers that may comprise the cell. The various layers applied to the opposed substrates are largely dependent upon the type of flow cell desired (i.e.. electrochemical, optical or combination elec-

TABLE 1

| ENZYMES | SOLID PHASES | RESINS | OPTIONAL INGREDIENTS |
|---|---|---|---|
| glucose oxidase, glutamate oxidase, lactate oxidase, glycerol phosphate oxidase, cholesterol oxidase, cholesterol esterase, lipase, glycerol kinase, glutamate dehydrogenase, creatinine deaminase, and uricase | agarose and derivatives thereof, polyacrylamide and derivatives thereof, silicas, aluminosilicates, aluminum oxides, carbon or graphite particles, and platinum group metal oxides | acrylic latex, styrene acrylic latexes, vinyl acetate latex and polyurethane latex | plasticizers, film forming agents, thickeners, stabilizers, dispersing agents, and defoaming agents | trochemical and optical). After the various layers have been applied, the substrates can be coupled to each other to form the flow cell which then can be interfaced with detection means for detecting a signal generated by the immobilized reagent means and flow means for introducing sample into the flow cell's flow channel. The substrates can be layered with the various layers described herein using any means capable of applying a consistently thick layer. Examples of such means include, but are not intended to be limited to stenciling, spray painting, tampo printing, photolithography, and the like, preferably screen printing. For example, in the case of an electrochemical flow cell, it has been found advantageous to screen print the following successive layers to one substrate: a reference electrode, a working electrode, a mask layer, a spacing layer and an adhesive layer; while applying a counter electrode layer to a second substrate. The two substrates and their respective layers can then be, for example, laminated to each other to form the flow cell. It will be understood, of course, that many variations, in terms of the possible order of layers and combinations of layers, are possible.

Advantageously, the flow cell can be mass produced by layering, for example, sheets or rolls of substrate material with the various layers described herein. The sheets or rolls of layered substrate can be stored at any of the stages of the layering process. For example, in the case of an electrochemical flow cell, sheets of substrate material can be layered with a reference electrode and a working electrode and stored before subsequent layers, for example a mask layer and an adhesive layer, are applied thereon. After all of the desired layers have been applied to the substrate material, they can be, for example, cut from the rolls or sheets of substrate material and assembled to form the diagnostic flow cell herein provided.

IV. DETECTION MEANS

Detection means for detecting an electrochemical response to the presence of an analyte that may be contained in a test sample include, but are not intended to be limited to potentiostats, potentiometers, and the like. Such detection means can be placed in communication with the flow cell using methodologies well known in the art. For example, an electrochemical flow cell can be placed in communication, or interfaced, with the detection means using electrical connectors such as wires and clamps.

Detection means for detecting an optical response to the presence of an analyte that may be contained in a test sample include, but are not intended to be limited to luminometers, spectrophotometers, and the like. Such detection means can be interfaced with suitable detection means using methodologies well known in the art. For example, an optically based flow cell can be interfaced with detection means using fiber optic cables.

It will be understood, of course, that the detection means employed is largely dependent upon the analyte being detected and therefore, the immobilized reagent means employed. It will also be understood that multiple detection means can be interfaced with the flow cell.

V. FLOW MEANS

Additionally, it will be obvious to one of skill in the art, that the flow cell can be connected to flow means which can transport samples into and out of the flow cell's flow channel. Examples of suitable flow means include, but are not intended to be limited to syringes, syringe pumps, reciprocating pumps, diaphragm pumps, pressure or vacuum sources and the like, preferably peristaltic pumps.

VI. EMBODIMENTS

While many types of devices fall within the scope of the present invention, particularly preferred embodiments will be described in conjunction with the drawings. Referring now to the drawings, FIG. 1 shows an expanded view of an electrochemical flow cell. FIG. 1 shows substrate 10 and the several layers that can be applied thereon to form one part of an electrochemical flow cell. Specifically, the layers that can be applied to the substrate 10 include: the reference electrode including redox couple 22 and conductive trace 32; the conductive traces 30 which form part of the working electrodes; a mask layer 40; a spacing layer 50; and an adhesive layer 60. FIG. 1 also shows a second substrate 70 and a counter electrode 80 which can be layered on substrate 70 to form the other half of an electrochemical flow cell. To assist in coupling the substrates to form the electrochemical flow cell, opposed substrates 10 and 70 are provided with alignment apertures 12 and 14, and 72 and 74; the mask layer 40 is provided with alignment apertures 42 and 44; the spacing layer is provided with alignment apertures 52 and 54; the adhesive layer is provided with alignment apertures 62 and 64; and the counter electrode is provided with alignment apertures 82 and 84.

Adhesive layer 60 and spacing layer 50 are supplied with longitudinal voids 66 and 56 which partially define the flow cell's flow channel when the adhesive and spacing layers are sandwiched between substrates 10 and 70. Substrate 70 and counter electrode layer 80 are supplied with port apertures 76, 78, 86 and 88. When the substrates, and their respective layers, are assembled or coupled to each other, the port apertures align near the ends of the longitudinal voids 56 and 66, and serve as inlet and outlet ports for the flow channel.

As seen best in FIG. 1, mask layer 40 is supplied with a plurality of apertures 46 equal to the number of conductive traces. When the flow cell is assembled, these apertures allow portions of the conductive traces 30 and redox couple 22 to remain exposed. Prior to coupling the substrates, an enzyme can be immobilized on the exposed portions of the conductive traces 30 to complete the working electrodes.

Figure 2:
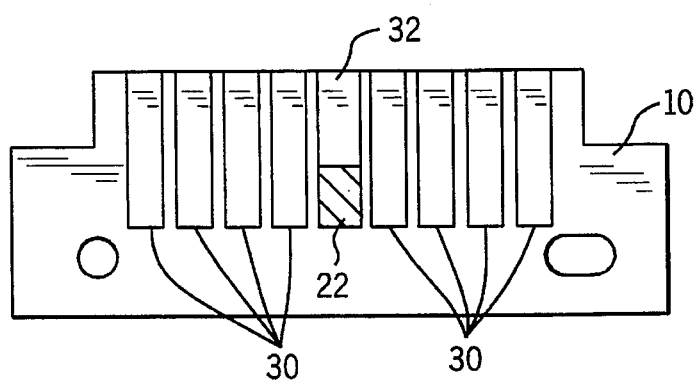
FIG. 2 illustrates a partially completed electrochemical flow cell.

FIG. 2 shows substrate 10 with the layers comprising the reference electrode (22 and 32) and the conductive traces 30 immobilized thereon. A portion of the redox couple 22 is exposed such that when the flow cell is assembled and a test sample is contained within the flow channel, the exposed portion of the redox couple can contact the test sample and maintain its potential.

Figure 3:
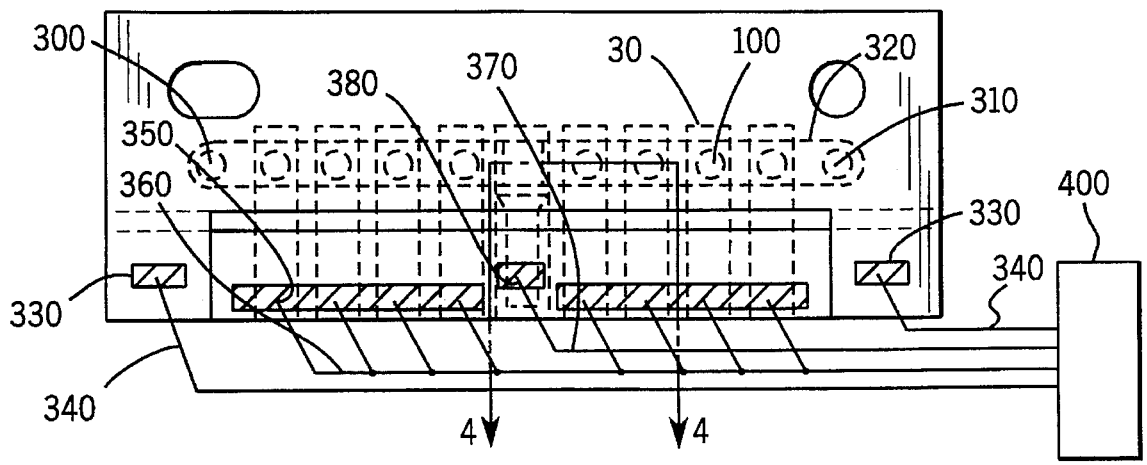
FIG. 3 illustrates an assembled electrochemical flow cell which is interfaced with detection means.

FIG. 3 shows an assembled electrochemical flow cell which is interfaced with potentiostat 400. As shown in FIG. 3, the flow cell is interfaced with the potentiostat via a series of electrical connections leading from the counter electrode, working electrodes and reference electrode to the potentiostat. Specifically, connections 330 and wires 340 interface the counter electrode and the potentiostat, connections 350 and wires 360 interface the working electrodes and the potentiostat, and connection 380 and wire 370 interface the reference electrode and the potentiostat. All connections are made with the conductive traces comprising the various electrodes.

FIG. 3 also shows a complete working electrode comprising immobilized enzyme 100 and conductive trace 30. Additionally inlet and outlet ports 300 and 310 are shown near the ends of flow channel 320.

Figure 4:
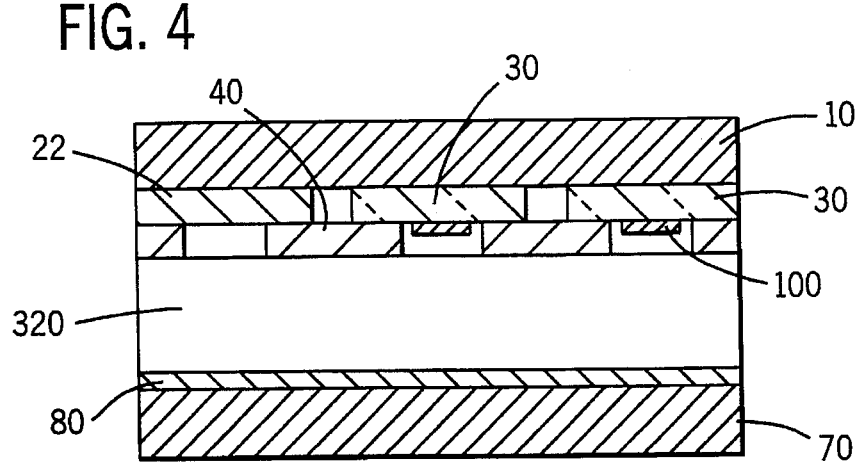
FIG. 4 illustrates a cross sectional view of an assembled electrochemical flow cell.

FIG. 4 shows a cross-sectional view of an electrochemical flow cell as taken through segment A-A of FIG. 3. As shown from that view, several of the layers which can form an assembled electrochemical flow cell can be seen. Included in the layers observable from this view are the substrates 10 and 70; redox couple 22; the working electrode including conductive traces 30 and the enzyme immobilized thereon 100; and the counter electrode 80. The flow channel 320 is also illustrated by FIG. 4.

Figure 5:
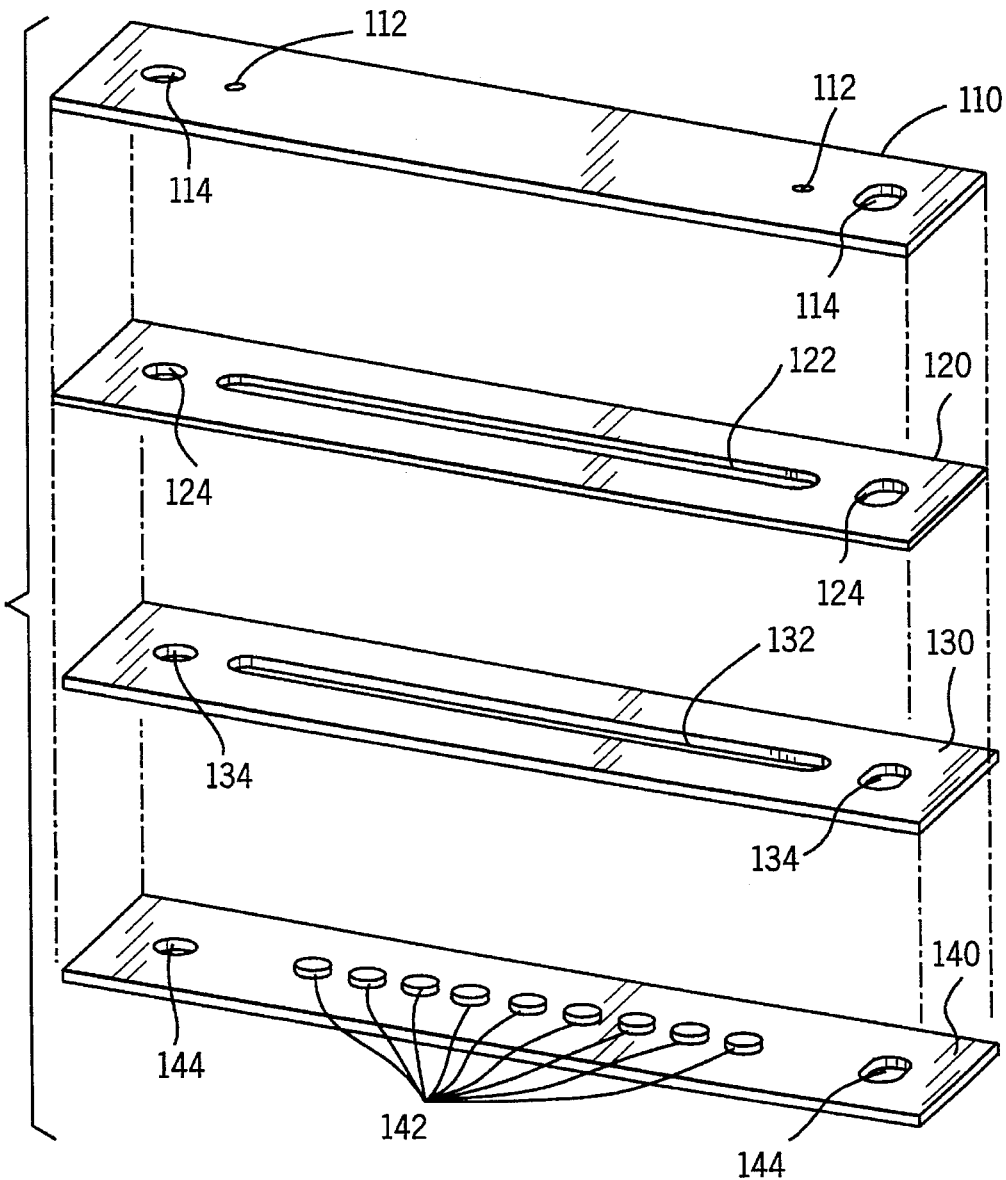
FIG. 5 illustrates an expanded view of an optical flow cell.

The various layers that can comprise an optical flow cell can be seen best in FIG. 5. FIG. 5 shows two substrate layers 110 and 140 and the layers that can be placed therebetween. Substrate 110 is supplied with apertures 112 which, when the flow cell is assembled, are located near the ends of longitudinal voids 122 and 132, and serve as inlet and outlet ports for the assembled optical flow cell's flow channel. Adhesive layer 120 is shown between substrate 110 and spacing layer 130 but would be equally effective between substrate 140 and spacing layer 130. The adhesive layer 120 and the spacing layer 130 have longitudinal voids, 122 and 132, respectively which help define the flow cell's flow channel when sandwiched between substrates 110 and 140. Also shown in FIG. 5 are a plurality of dye spots 142 which are immobilized on substrate 140. The substrates 110 and 140, the adhesive layer 120 and the spacing layer 130 are also supplied with alignment apertures 114, 144, 124 and 134 which assist in aligning the flow cell during assembly.

Figure 6:
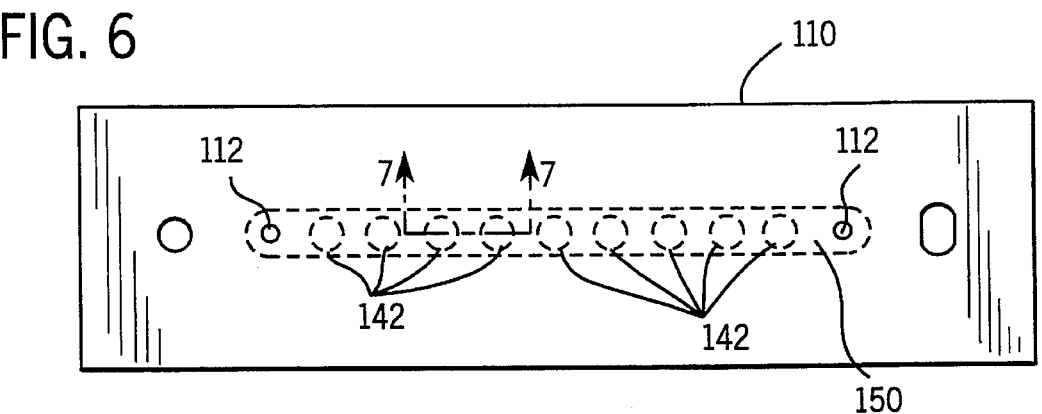
FIG. 6 illustrates an assembled optical flow cell.

FIG. 6 illustrates an assembled optical flow cell including substrate 110; dye spots 142; and apertures 112 which serve as inlet and outlet ports for the flow channel 150.

Figure 7:
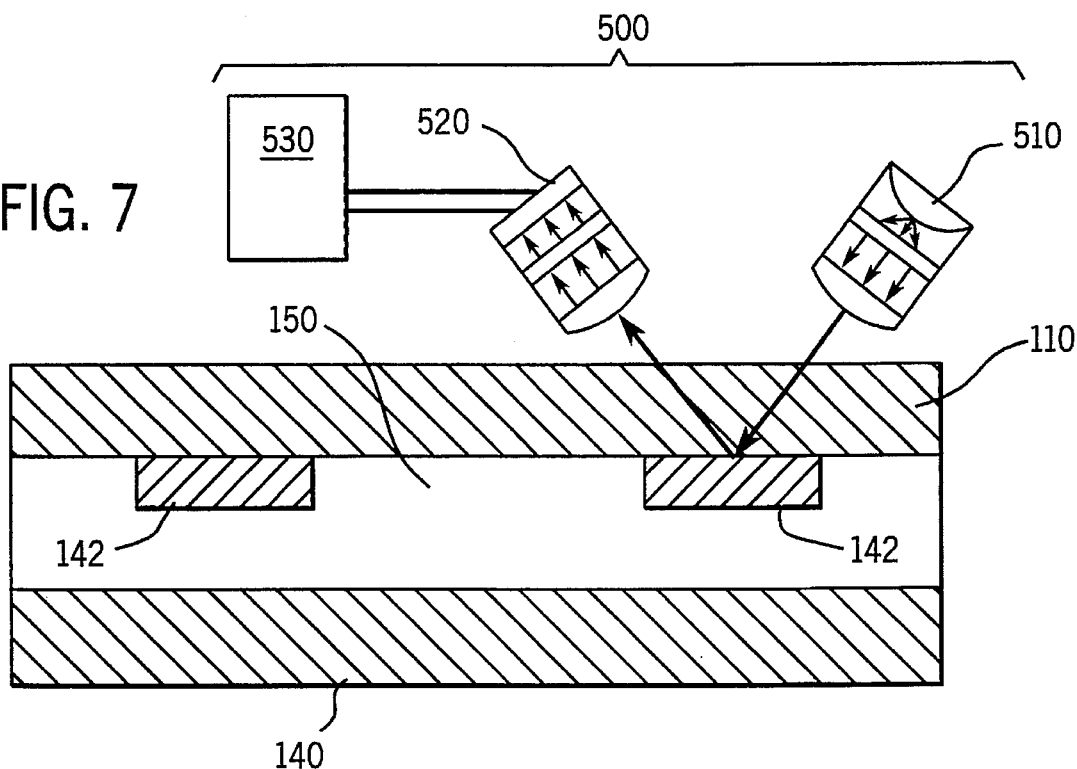
FIG. 7 illustrates a cross sectional view of an assembled optical flow cell.

FIG. 7 shows a cross sectional view, as taken through section B-B of FIG. 6, of an optical flow cell that is interfaced with detection means 500. As shown by FIG. 7, the dye spots 142 are contained in the flow channel 150 which is defined by substrates 110 and 140; and the longitudinal void in the spacing layer (not observable from this perspective). As shown in FIG. 7, the detection means 500 can comprise a light source 510, a light detector 520 and a intensity reader 530.

VII. ASSAY METHODS

The flow cell device can be used to detect the presence or amount of an analyte which may be present in a test sample. A test sample can be introduced into the flow cell's flow channel wherein it contacts the immobilized reagent means. The presence or amount of the analyte can be determined as a result of the analyte contacting the immobilized reagent means. When contacted with the test sample, the immobilized reagent means generates a detectable signal that is detected by detection means and is indicative of the presence or amount of analyte that may be contained in the test sample. It will be understood, of course, that the test sample can be, for example, introduced into the flow cell's flow channel and stopped therein, it can be continuously flowed through the flow channel or it can be recirculated through the flow channel.

The following examples are not intended to limit the invention herein provided but are intended to illustrate the invention.

EXAMPLE 1

Production of an Bioreagent Immobilization Medium Using Glucose Oxidase Adsorbed to Platinized Carbon The enzyme binding resin (see below) was selected from the commercial paint industry formulations designed to be fast drying, adherent and able to emulsify pigments. The mixing procedure was designed to generate high shear rates, thus producing a very highly dispersed pigment and small particle size. In order to obtain this smooth emulsion, the formulation components were mixed in a WIG-L-BUG (Crescent Dental Manufacturing, Lyons, Ill.) which is a device designed to mix dental amalgams. The mixer mechanically agitates the formulation in a 2 ml stainless steel vial containing a ball bearing, thus allowing 0.5 to 1 ml coating preparations to be blended.

Materials

1. Platinized Vulcan XC 72 (carbon black) containing 10% platinum
2. Glucose Oxidase (GOD: Grade I from Aspergillus niger, Boehringer Mannheim Biochemicals, Indianapolis, Ind.)
3. Phosphate Buffered Saline (PBS: 100 mM sodium Phosphate, 100 mM NaCl, pH 6.0)
4. Acrylic resin mix (31.6% non-volatile solids formulated as shown below)

| Acrylic Resin Mix Component | % by weight |
|---|---|
| Joncryl 537 acrylic emulsion (Johnson Wax, Racine, WI) | 54 |
| Joncryl 56 acrylic resin (Johnson Wax, Racine, WI) | 27 |
| DMAMP 80 (Angus Chemical Co., Northbrook, IL) | 1 |
| Ektasolve EP (Eastman Chemicals, Kingsport, TN) | 9 |
| Distilled water | 9 |

Procedure

Enzyme was adsorbed to platinized carbon by adding a solution of GOD in PBS buffer to suspensions of platinized carbon in PBS buffer. One suspension contained 101 mg of platinized carbon in 0.44 ml of PBS plus 0.2 ml of a 50 mg/ml solution of GOD, while the other suspension contained 51 mg of platinized carbon in 0.2 ml of PBS plus 0.1 ml of a 50 mg/ml solution of GOD. The mixtures were allowed to statically incubate for 1.5 hours at an ambient temperature before they were centrifuged at 2000 rpm. The supernatants were discarded and the resulting wet GOD/carbon pellets were resuspended in 0.8 gm of the resin mix and blended in a WIG-L-BUG for 10 minutes. A WIG-L-BUG (Crescent Dental Manufacturing, Lyons, Ill.) is a device designed to mix dental amalgams. The mixer mechanically agitates the formulation in a 2 ml stainless steel vial containing a ball bearing, thus allowing 0.5 to 1 ml coating preparations to be blended. The resulting coating solutions were hand dispensed onto separate electrodes and tested electrochemically. The formulation for the coating solution is shown below in Table 2.

TABLE 2

| Formula | mg carbon | mg Resin Mix | mg Resin Solids | Resin solids/Carbon ratio |
|---|---|---|---|---|
| 1 | 101 | 800 | 253 | 2.50 |

EXAMPLE 2

Electrochemical Flow Cell

Materials:
1. ICI ST505 Heat Stabilized Polyester Film (Tekra Corporation, Milwaukee, Wisc.)
2. Acheson SS24950 Silver/Silver Chloride Ink (Acheson Colloids, Port Huron, Mich.)
3. Acheson 423SS Carbon Ink (Acheson Colloids, Port Huron, Mich.)
4. Acheson ML25198 Insulating Dielectric (Acheson Colloids, Port Huron, Mich.)
5. Acheson UV 8002 Adhesive (Acheson Colloids, Port Huron, Mich.)
6. Bioreagent Immobilization Medium (from Example 1)
7. Potentiostat—an eight channel potentiostat was assembled at Abbott Laboratories (Abbott Park, Ill.) to accommodate the flow cell described herein Manufacturing Procedure:

A 0.007 inch thick polyester film was used as substrate support material for both halves of the flow cell. A working electrode, reference electrode, mask layer, spacing layer and adhesive were applied to one substrate and a counter electrode was applied to the other substrate. The manufacturing process will be explained with references to FIG. 1. A layer of silver/silver chloride ink 22 was screen printed in a pattern to form the redox couple portion of a single reference electrode. Next, a layer of carbon ink was screen printed on the redox couple and substrate in a pattern to form eight working electrode conductive traces 30 and the conductive trace portion 32 of the reference electrode. The redox couple layer and conductive trace layers were printed with quantities of the respective materials that were sufficient to provide an end to end resistance of less than 100 ohms.

On top of both the silver/silver chloride ink and carbon ink layers a layer of dielectric 40 was screen printed in a pattern to mask all of the working conductive traces 30 and redox couple 22 except for a small circular area 46 which was 0.066 inches in diameter. The masking layer of dielectric was applied in a quantity sufficient to become water impermeable. A layer of dielectric was then applied to the mask layer in a pattern to form the spacing layer 50 having longitudinal void 56. The spacing layer of dielectric was applied using a quantity sufficient to give the flow cell's flow channel a 10 µl/cm$^2$ volume. A 0.001 inch layer of adhesive 60 was then printed on top of the spacing layer. The adhesive layer also had longitudinal void 66. A paper release liner was added to the surface of the adhesive to protect it during handling. A steel ruled die was then used to cut this part of the device from the sheet of polyester film. A steel ruled die was also used to simultaneously cut alignment apertures 12, 14, 42, 44, 54, 62 and 64 from all layers printed on the polyester film.

Again, with reference to FIG. 1, the second substrate of the flow cell was prepared by screen printing a layer of carbon ink 80 (counter electrode) onto a sheet of polyester film. The quantity of carbon ink used was sufficient to provide an end to end resistance of less than 100 ohms. The outline of this part of the flow cell, the alignment apertures and the fluid inlet and outlet ports were cut from the sheet of polyester film with a steel-ruled die.

After the substrates and the layers immobilized thereon were cut from the polyester film, 0.35 µl of bioreagent immobilization medium (from Example 1) was dispensed onto the circular area of the eight working electrode traces 30. The bioreagent was allowed to cure at room temperature for one hour. Using a jig and alignment pins, the two substrates were aligned and laminated together.

Testing Procedure:

The testing procedure will be described with reference to FIG. 3. The assembled flow cell was placed on a stand and connected to a peristaltic pump (not shown) via fluid connections to the inlet and outlet ports 300 and 310. Electrical connections (between the flow cell and potentiostat 400) to all eight of the working electrodes 30, the counter electrode (not shown) and the reference electrode 54 were made using clamps and wires 350 and 360; 330 and 340; and 360 and 370 respectively. Liquids were drawn through the cell with a peristaltic pump and the potential of the electrodes relative to one another was controlled by a three electrode potentiostat with eight separate current monitoring channels.

The working electrode potential was set at 350 mV versus the on board Ag/AgCl reference electrode. Solutions of differing glucose concentrations were then successively drawn through the cell and the current which passed at each of the eight working electrodes was monitored and recorded.

Figure 8:
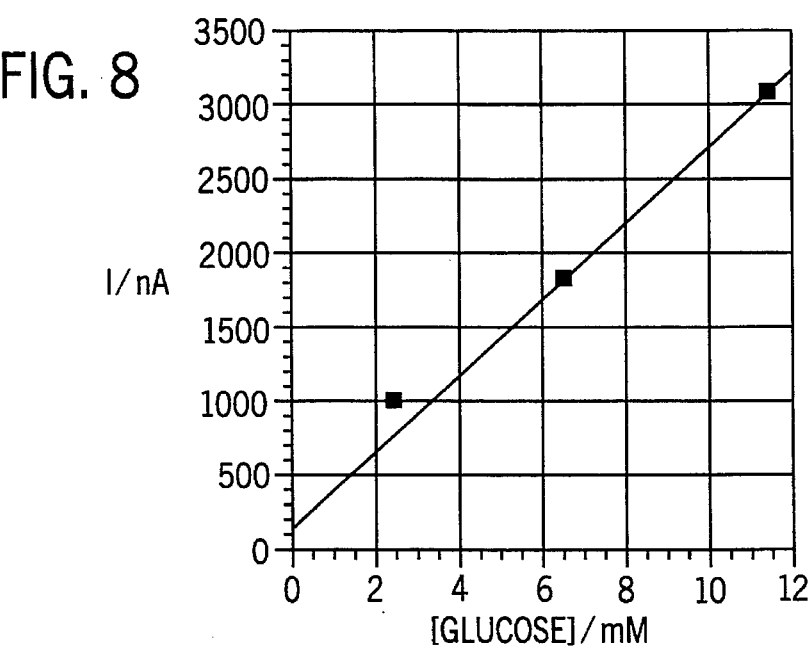
FIG. 8 graphically illustrates an electrochemical flow cell's working electrode response to varying concentrations of glucose.

The graph shown in FIG. 8 illustrates the current response of one of the working electrodes to 0 mM, 2.5 mM, 6.5 mM and 11.4 mM glucose solutions in pH 7.5 aqueous phosphate buffer (PBS—40.5 mM $Na_2HPO_{4, 9.5}$ mM $NaH_2PO_{4, 50}$ mM NaCl). Also shown in FIG. 8 is the linear regression through the four data points.

As shown by FIG. 8 the electrode response varies linearly with the glucose concentration in the test sample.

EXAMPLE 3

Preparation of an Oxygen Sensitive Dye

Free base tetra(pentafluorophenyl)porphyrin [$H_2$(TFPP)] was made by adding 2.0 ml of pentafluorobenzaldehyde, 1.5 ml pyrole and 2.0 ml of boron trifluoride etherate to 1500 ml dichloromethane to form a reaction mixture. All materials comprising the reaction mixture are available from Aldrich Chemical Co., Inc., Milwaukee, Wisc. The reaction mixture was stirred for 1 hour before 2.5 grams of 2,3-dichloro-5, 6-dicyano-1,4-benzoquinone (Sigma, ST. Louis, Mo.) was added and the resulting mixture was heated to 40° C. for 1 hour. Then, the solvent was flash dried and the crude solid $H_2$(TFPP) product was chromatographed over silica gel using dichloromethane as the eluting solvent. 1.0 gram of the purified $H_2$(TFPP) and a 10 times molar excess of $PtCl_2$ (Aldrich Chemical Co. Inc.) were refluxed for 24 hours in 500 ml of benzonitrile to synthesize crude platinum tetra-(pentafluorophenyl)porphyrin [Pt(TFPP)]. The product was purified on a neutral alumina column using $CH_2Cl_2$ as the eluant. An oxygen sensitive dye solution was prepared by dissolving 100 mg of the purified Pt(TFPP) in a 25 ml of a silicone polymer stock solution. The polymer stock solution was made by dissolving 10.0 grams of a dimethylsiloxane-bisphenol (General Electric Inc., Waterford, N.Y.) in 100 ml tetrahydrofuran.

EXAMPLE 4

Optical Flow Cell

Materials:
1. ICI ST505 Heat Stabilized Polyester Film (Tekra Corporation, Milwaukee, Wisc.)
2. Acheson ML25198 Insulating Dielectric (Acheson Colloids, Port Huron, Mich.)
3. Acheson SU459 Adhesive (Acheson Colloids, Port Huron, Mich.)
4. Platinum tetra(pentafluorophenyl)porphyrin from Example 3.

Manufacturing Procedure:

The manufacturing procedure will be described with reference to FIG. 5. A layer of dielectric ink 130 was screen printed onto a substrate 140, which comprised a sheet of polyester film, to form the spacing layer of the flow cell. The spacing layer of dielectric was applied using a quantity sufficient to give the flow cell's flow channel a 10 µl/cm$^2$ volume. A 0.001 inch layer of adhesive 120 was then screen printed on top of the dielectric layer in the pattern shown in FIG. 5. A release liner was then applied onto the surface of the adhesive to protect it during handling. The outline of the cell and alignment apertures 114, 134 and 144 were then cut from the polyester sheet using a steel-ruled die. The other substrate was formed by cutting the cell outline, alignment apertures 114 and inlet and outlet ports 112 from a 0.007 inch thick sheet of polyester film.

After removing the release liner, 1.0 µl aliquots of the oxygen sensitive dye 142 (from Example 3) were then applied to substrate 140 such that the dye spots were aligned within the longitudinal voids 122 and 132. The dye was allowed to dry for one hour at room temperature and the polyester substrates were then positioned using an alignment jig and alignment pins before being laminated together.

Figure 9:
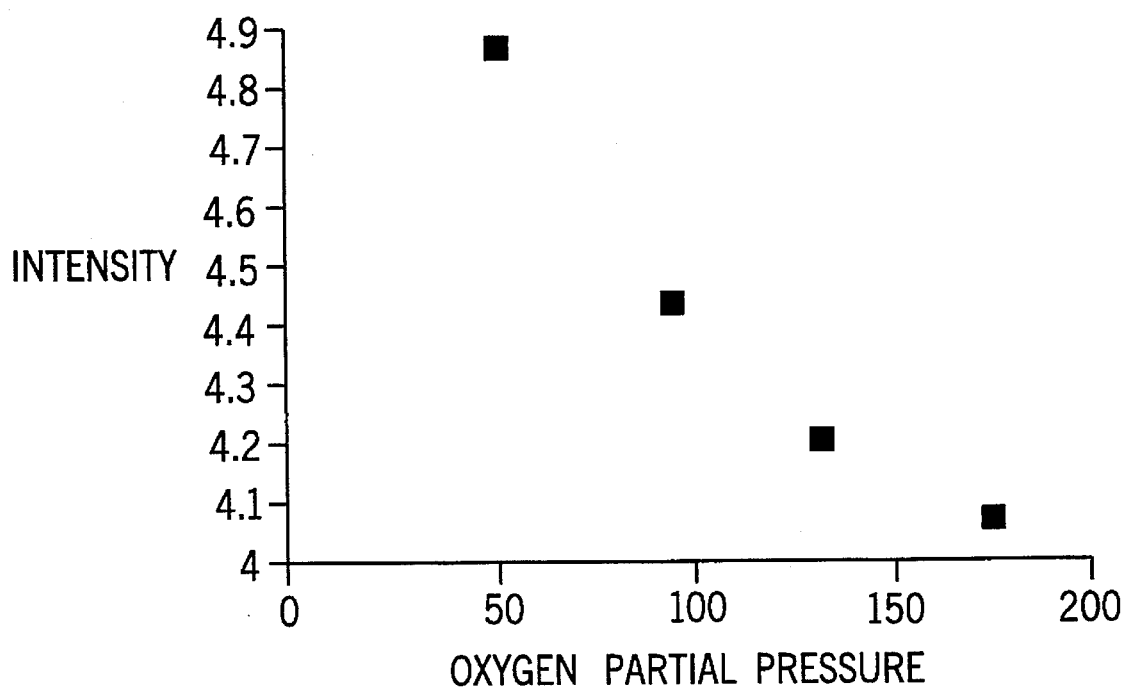
FIG. 9 graphically illustrates an optical flow cell's response to varying concentrations of dissolved oxygen.

Testing Procedure:

The assembled flow cell was fixed on a stand and fluid tubes were connected to the inlet and outlet ports. Tonometered solutions were then moved into and out of the cell using a peristaltic pump. Tests were performed by positioning a 250 µm optical fiber (Ensign-Bickford Optics Co.; Avon, Conn.) above the dye spots 142 and illuminating the dye with light emitted from a pulsed light emitting diode (Hewlet Packard Co., Cupertino, Calif.) while a solution of tonometered oxygen buffer was flowing through the flow channel. Using an avalanche photodetector (Hamamatsu Corp., Bridgewater, N.J.), phosphorescent intensity measurements were recorded in 2 time regions (3–17 µseconds and 3–200 µseconds) after each excitation pulse. The phosphorescent intensity ratio was calculated and plotted as a function of oxygen concentration. As shown by FIG. 9, a reproducible non-linear relationship between the intensity ratio and oxygen partial pressure is observed.

What is claimed is:

1. A multi flat-layered diagnostic flow cell for determining the presence or amount of an analyte in a test sample, said flow cell being reusable for a plurality of test samples, and comprising:

i) a hydrophobic spacing layer disposed between a first and a second opposed substrate, said first and second substrates being chemically inert and non-conductive, and wherein said spacing layer has a longitudinal void and wherein said spacing layer and said opposed substrates define a flow channel;

ii) fastening means for coupling said spacing layer and said opposed substrates;

iii) inlet means for permitting said sample to enter said flow channel;

iv) outlet means for permitting said sample to exit said flow channel; and v) means for producing a detectable signal, wherein said means is at least partially contained within said flow channel; said means comprising a working electrode containing an immobilized bioreagent enzyme dispersed within a latex resin binding reagent.

2. The flow cell of claim 1 wherein said first opposed substrate comprises a material selected from the group consisting of glass, silicon, polyester, polycarbonate, polystyrene, molded plastics and film plastics.

3. The flow cell of claim 1 wherein said second opposed substrate comprises a material selected from the group consisting of glass, silicon, polyester, polycarbonate, polystyrene, molded plastics and film plastics.

4. The flow cell of claim 1 wherein said spacing layer comprises a material selected from the group consisting of printing inks, latexes, urethanes, vinyls, polyesters, and combinations of one or more printing inks, latexes, urethanes, vinyls and polyesters.

5. The flow cell of claim 1 further comprising a hydrophobic mask layer disposed between said substrates.

6. The flow cell of claim 5 wherein said mask layer comprises a material selected from the group consisting of printing inks, latexes, urethanes, vinyls, polyesters and combinations of one or more printing inks, latexes, urethanes, vinyls and polyesters.

7. The flow cell of claim 1 wherein said fastening means is selected from the group consisting of a rivet, a nut and a bolt, a sonic weld and an adhesive.

8. The flow cell of claim 7 wherein said adhesive is selected from the group consisting of an ultraviolet cured pressure sensitive adhesive, a heat cured pressure sensitive adhesive and a pressure activated adhesive.

9. The flow cell of claim 1 wherein said fastening means is a polyurethane ultraviolet cured pressure sensitive adhesive.

10. The flow cell of claim 1 wherein said means for producing a detectable signal further comprises a reference electrode, and a counter electrode.

11. The flow cell of claim 10 wherein said reference electrode comprises a redox couple and a first conductive trace.

12. The flow cell of claim 11 wherein said redox couple is selected from the group consisting of silver/silver chloride/graphite, mercury/mercurous chloride, silver/silver iodide and silver/silver chloride.

13. The flow cell of claim 11 wherein said redox couple comprises silver/silver chloride.

14. The flow cell of claim 11 wherein said conductive trace comprises a material selected from the group consisting of carbon, gold, nickel, silver, palladium, ruthenium, rhodium, tin oxide, indium tin oxide and combinations of one or more of carbon, gold, nickel, silver, palladium, ruthenium, rhodium, tin oxide and indium tin oxide.

15. The flow cell of claim 11 wherein said conductive trace comprises graphite and screen printed ink.

16. The flow cell of claim 11 wherein said conductive trace is a flat layer.

17. The flow cell of claim 10 wherein said counter electrode comprises a material selected from the group consisting of carbon, gold, nickel, silver, palladium, ruthenium, rhodium, tin oxide, indium tin oxide and combinations of one or more of carbon, gold, nickel, silver, palladium, ruthenium, rhodium, tin oxide and indium tin oxide.

18. The flow cell of claim 10 wherein said counter electrode comprises graphite and screen printed ink.

19. The flow cell of claim 10 wherein said reagent means further comprises an optically active dye.

20. The flow cell of claim 19 wherein said dye is selected from the group consisting of a pH sensitive dye, an oxygen sensitive dye and an ion sensitive dye.

21. The flow cell of claim 19 wherein said dye comprises platinum tetra(pentafluorophenyl)porphyrin.

22. The flow cell of claim 10 wherein said working electrode comprises a second conductive trace.

23. The flow cell of claim 22 wherein said conductive trace comprises a material selected from the group consisting of carbon, gold, nickel, silver, palladium, ruthenium, rhodium, tin oxide, indium tin oxide and combinations of one or more of carbon, gold, nickel, silver, palladium, ruthenium, rhodium, tin oxide and indium tin oxide.

24. The flow cell of claim 22 wherein said conductive trace comprises graphite and screen printed ink.

25. The flow cell of claim 22, wherein said enzyme is immobilized to a solid phase material and is further immobilized to said conductive trace.

26. The flow cell of claim 25, wherein said enzyme is selected from the group consisting of glucose oxidase, glutamate oxidase, lactate oxidase, glycerol phosphate oxidase, cholesterol oxidase, cholesterol esterase, lipase, glycerol kinase, glutamate dehydrogenase, creatine deaminase, and uricase.

27. The flow cell of claim 26, wherein said latex resin is selected from the group consisting of acrylic latex, styrene acrylic latexes, vinyl acetate latex and polyurethane latex.

28. The flow cell of claim 27, wherein said solid phase material is selected from the group consisting of agarose and derivatives thereof, polyacrylamide and derivatives thereof, silicas, aluminosilicates, aluminum oxides, carbon or graphite particles, and platinum group metal oxides.

29. The flow cell of claim 22 wherein said conductive trace is a flat layer.

30. The flow cell of claim 1 wherein said reagent means comprises an optically active dye.

31. The flow cell of claim 30 wherein said dye is selected from the group consisting of a pH sensitive dye, an oxygen sensitive dye and an ion sensitive dye.

32. The flow cell of claim 30 wherein said dye comprises platinum tetra(pentafluorophenyl)prophyrin.

33. The flow cell of claim 1 wherein said flow cell further comprises flow means for introducing said test sample into said flow channel wherein said flow means is interfaced with said inlet and outlet means; and detection means for detecting a detactable signal wherein said detection means is interfaced with said immobilized reagent means.

34. The flow cell of claim 1, wherein said inlet means and said outlet means comprises a pair of apertures within said second substrate.

35. The flow cell of claim 34, wherein said apertures are aligned within said second substrate at opposite ends of said flow channel.

36. The flow cell of claim 1, wherein said enzyme is selected from the group consisting of glucose oxidase, glutamate oxidase, lactate oxidase, glycerol phosphate oxidase, cholesterol oxidase, cholesterol esterase, lipase, glycerol kinase, glutamate dehydrogenase, creatine deaminase, and uricase.

37. The flow cell of claim 36, wherein said latex resin is selected from the group consisting of acrylic latex, styrene acrylic latexes, vinyl acetate latex and polyurethane latex.

38. A multiflat-layered diagnostic flow cell for determining the presence or amount of one or more analytes in a test sample, said flow cell being reusable for a plurality of test samples, and comprising:

i) a hydrophobic spacing layer disposed between a first and second opposed substrate, said first and second substrates being chemically inert and non-conductive, and wherein said spacing layer has a longitudinal void and wherein said spacing layer and said opposed substrates define a flow channel;

ii) fastening means for coupling said spacing layer and said opposed substrates;

iii) inlet means for permitting said sample to enter said flow channel;

iv) outlet means for permitting said sample to exit said flow channel; and v) means for producing a detectable signal, wherein said means is at least partially contained within said flow channel; said means comprising a working electrode containing at least one immobilized bioreagent dispersed within a latex resin binding reagent.

39. The flow cell of claim 38 wherein working electrode comprises a conductive trace which is a flat layer.

* * * * *

UNITED STATES PATENT AND TRADEMARK OFFICE
CERTIFICATE OF CORRECTION

PATENT NO. : 5,520,787
DATED : May 28, 1996
INVENTOR(S) : T. J. Hanagan, et. Al.

It is certified that error appears in the above-indentified patent and that said Letters Patent is hereby corrected as shown below:

Column 11, line 33, change "14, 42, 44, 54, 62" to --14, 42, 44, 52, 54, 62--.

Column 12, line 4, change "$9.5$ mM" to --9.5 mM--.

Column 12, line 4, change "$50$ mM" to --50 mM--.

Signed and Sealed this

Nineteenth Day of November, 1996

Attest:

BRUCE LEHMAN

*Attesting Officer*  *Commissioner of Patents and Trademarks*